US005986052A

United States Patent [19]
Goetinck et al.

[11] Patent Number: 5,986,052
[45] Date of Patent: Nov. 16, 1999

[54] FUSION POLYPEPTIDE CONTAINING FRAGMENTS OF CARTILAGE MATRIX PROTEIN AND LINK PROTEIN

[75] Inventors: Paul F. Goetinck, Boston; M. Mehrdad Tondravi, Marshfield, both of Mass.; Francois Binette, Plainsboro, N.J.

[73] Assignee: The General Hospital Corporation, Boston, Mass.

[21] Appl. No.: 08/463,218

[22] Filed: Jun. 5, 1995

Related U.S. Application Data

[62] Division of application No. 08/001,078, Jan. 6, 1993, Pat. No. 5,872,094.

[51] Int. Cl.$^6$ .............................. C07K 1/00; C07K 17/02; C12N 15/00; C12N 11/02
[52] U.S. Cl. .......................... 530/350; 424/422; 424/520; 435/172.3; 435/174; 435/180; 435/181; 514/2; 530/300; 530/353; 530/395; 530/402; 530/810; 530/815
[58] Field of Search .............................. 435/172.3, 174, 435/179, 180, 181; 530/300, 350, 395, 402, 810, 815, 353; 935/11; 424/422, 520; 514/2

[56] References Cited

U.S. PATENT DOCUMENTS

| | | | |
|---|---|---|---|
| 4,778,468 | 10/1988 | Hunt et al. | 623/16 |
| 4,801,619 | 1/1989 | Lindblad | 514/825 |
| 5,114,844 | 5/1992 | Cohen et al. | 435/7.21 |
| 5,202,247 | 4/1993 | Kilburn et al. | 435/179 X |
| 5,686,059 | 11/1997 | Goetinck et al. | 424/9.1 |

FOREIGN PATENT DOCUMENTS

WO93/21226  10/1993  WIPO .

OTHER PUBLICATIONS

Stripe et al., Development 107:23–33, 1989.
Stripe et al., J. Cell. Biol. 93:910, 1982.
Agraves et al. "Structural features of cartilage matrix protein deduced from cDNA" *PNAS USA* 84:464–468 (1987).
Binnette et al. "Link Protein is a ubiquitous structural component of non-cartilaginous tissues" *Molecular Biology of the Cell* 3:224a, Abstract No. 1299 (1992).
Bonnet et al. "An unexpected sequence homology between link proteins of the proteoglycan complex and immunoglobulin–like proteins" *Biochem Biophys. Acta.* 873:152–155 (1986).
Caterson et al. "Monoclonal Antibodies as Probes for Determining the Microheterogeneity of the Link Proteins of Cartilage Proteoglycan" *J. Biol. Chem.* 260:11348–11356 (1985).
Deák et al. "Complete amino acid sequence of chicken cartilage link protein deduced from cDNA clones" *PNAS USA* 83:3766–3770 (1986).
Doege et al. "Link protein cDNA sequence reveals a tandemly repeated protein structure" *PNAS USA* 83:3761–3765 (1986).

Dudhia and Hardingham "The primary structure of human cartilage link protein" *Nucl. Acids Res.* 18:1292 (1990).
Gardell et al. "Link Protein and a Hyaluronic Acid–Binding Region as Components of Aorta Proteoglycan" *Biochem. Biophys. Res. Comm.* 95:1823–1831 (1980).
Goetinck et al. "Macromolecular Organization of the Extracellular Matrix of Cartilage" *Cell Lineages in Development* 599:29–37 (1990).
Goetinck et al. "The Tandemly Repeated Sequences of Cartilage Link Protein Contain the Sites for Interaction with Hyaluronic Acid" *J. Cell. Biol.* 105:2043–2048 (1987).
Howell et al. "A Mini Review: Proteoglycan Aggregate Profiles in the Pond–Nuki Dog Model of Osteoarthritis and in Canine Disuse Atrophy" *British Journal of Rheumatology* 31(Suppl. 1):7–11 (1992).
Jenkins et al. "Structure and Chromosomal Location of the Human Gene Encoding Cartilage Matrix Protein" *J. Biol. Chem.* 265:19624–19631 (1990).
Keiser et al. "Degradation of Cartilage Proteoglycan by Human Leukocyte Granule Neutral Proteases—A Model of Joint Injury" *Journal of Clinical Investigation* 57:625–632 (1976).
Kiss et al. "Structure of the Gene for Cartilage Matrix Protein, a Modular Protein of the Extracellular Matrix" *J. Biol. Chem.* 264:8126–8134 (1989).
Lord et al. "Interaction of Proteoglycan with Cartilage Matrix Protein" *Fed. Proc.* 43:1695a, Abstract No. 1626 (1984).
Martel–Pelletier et al. "Activation of neutral metalloprotease in human osteoarthritic knee cartilage: evidence for degradation in the core protein of sulphated proteoglycan" *Annals of the Rheumatic Diseases* 47:801–808 (1988).
Neame et al. "An Amino Acid Sequence Common to Both Cartilage Proteoglycan and Link Protein" *J. Biol. Chem.* 260:12402–12404 (1985).

(List continued on next page.)

*Primary Examiner*—David M. Naff
*Attorney, Agent, or Firm*—Fish & Richardson, P.C.

[57] ABSTRACT

Link protein and cartilage matrix protein, which are two major components of the extracellular cartilage matrix, have been found to bind to each other. Polypeptide fragments of cartilage matrix protein and link protein are produced. A recombinant fusion polypeptide is prepared containing a fragment of cartilage matrix protein that binds to link protein and a fragment of link protein that binds to cartilage matrix protein. The cartilage matrix protein fragment may bind to collagen and contain the CMP-1 or CMP-2 domain, and the link protein may bind to a complex of hyaluronic acid and proteoglycan. The fragments or fusion polypeptide can be administered for repair of diseased or injured cartilaginous and non-cartilaginous tissue by promoting binding of a complex of proteoglycan and hyaluronic acid to collagen. The fragments or fusion polypeptide can be anchored to the surface of a prosthetic device, implant or tissue graft to promote adherence of tissue and biocompatibility. By anchoring a fragment of cartilage matrix protein or link protein on a surface, cartilaginous tissue, cartilage matrix protein or link protein may be attached to the surface.

4 Claims, 5 Drawing Sheets

OTHER PUBLICATIONS

Neame et al. "The Primary Structure of Link Protein from Rat Chondrosarcoma Proteoglycan" *J. Biol. Chem.* 261:3519–3535 (1986).

Paulsson et al. "Purification and structural characterization of a cartilage matrix protein" *Biochem. J.* 197:367–375 (1981).

Poole et al. "Mammalian Eyes and Associated Tissues Contain Molecules That Are Immunologically Related to Cartilage Proteoglycan and Link Protein" *J. Cell. Biol.* 93:910–920 (1982).

Rhodes et al. "Characterization of the promoter for the rat and human link protein gene" *Nuc. Acids Res.* 19:1933–1939 (1991).

Ripellino et al. "Immunoelectron Microscopic Localization of Hyaluronic Acid–binding Region and Link Protein Epitopes in Brain" *J. Cell. Biol.* 108:1899–1907 (1989).

Stirpe and Goetinck "Gene regulation during cartilage differentiation: temporal and spatial expression of link protein and cartilage matrix protein in the developing limb" *Development* 107:23–33 (1989).

Stirpe et al. "The Chicken Embryonic Mesonephros Synthesizes Link Protein, an Extracellular Matrix Molecule Usually Found in Cartilage" *Developmental Biology* 137(2):419–424 (1990).

Tsonis et al. "Expression of Cartilage–Matrix Genes and Localization of Their Translation Products in the Embryonic Chick Eye" *Experimental Eye Research* 46:753–764 (1988).

Winterbottom et al. "Cartilage Matrix Protein is a Component of the Collagen Fibril of Cartilage" *Developmental Dynamics* 193:266–276 (1992).

Chandrasekhar et al., "In Vitgro Regulation of Cartilage Matrix Assembly By A Mr 54,000 Collagen–binding Protein", PNAS USA 83:5126–5130 (1986).

```
MRVLSGTSLMLCSLLLLLQALCSPGLAPQSRGHLCRTRPTDLVFVVDSSRSVRPVEFEKVKVFLSQVIESLDVGPNATRVGMVNYASTVKQEFSLRAHVS    100
KAALLQAVRRIQPLSTGTMTGLAIQFAITKAFGDAEGGRSRSPDISKVVIVVTDGRPQDSVQDVSARARASGVELFAIGVSVDKATLRQIASEPQDEHV    200
DYVESYSVIEKLSRKFQEAFCVVSDLCATGDHDCEQVCISSPGSYTCACHEGFTLNSDGKTCNVCSGGGGSSATDLVFLIDGSKSVRPENFELVKKFISQ   300
IVDTLDVSDKLAQVGLVQYSSSVRQEFPLGRFHTKKDIKAAVRNMSYMEKGTMGAALKYLIDNSFTVSSGARPGAQKVGIVFTDGRSQDYINDAAKKAK    400
DLGFKMFAVGVGNAVEDELREIASEPVAEFYFYTADFKTINQIGKKLQKKICVEEDPCACESLVKFQAKVEGLLQALTRKLEAVSKRLAILENTVV        496

(SEQ ID NO:1)
```

FUSION POLYPEPTIDE CONTAINING FRAGMENTS OF CARTILAGE MATRIX PROTEIN AND LINK PROTEIN

This application is a divisional application of Ser. No. 08/001,078 filed on Jan. 6, 1993, now U.S. Pat. No. 5,872, 094. The contents of all of the aforementioned application is hereby incorporated by reference.

STATEMENT AS TO FEDERALLY SPONSOTRED RESEARCH

Partial funding of the work described herein was provided by grants HD-22016 and HD-22050 awarded by the National Intitutes of Health, and the United States Government has certain rights to the invention.

BACKGROUND OF THE INVENTION

The invention relates to the extracellular matrix of cartilage, and more specifically to cartilage matrix protein (CMP) and link protein (LP).

Connective tissues, in general, have an abundant extracellular matrix, synthesized and maintained by specialized cells. The interactions among these cells, the uniquely combined extracellular matrix components, and the water, electrolytes, and proteins in the extracellular fluid of each type of connective tissue determine the tissue's functional characteristics.

In cartilage, one major component of the extracellular matrix is the collagen fibril. As the principal tensile element, the collagen fibril plays a key role in the structural stabilization of cartilaginous tissues. The fibril consists of a core of type XI collagen surrounded by type II collagen, and on the periphery there is type IX collagen covalently attached to the type II collagen (Mendler et al. *J. Cell Biol.* 108: 191–197, 1989).

Several non-collagenous proteins that interact with collagen fibrils, including decorin (Vogel et al., *Coll. Rel. Res.* 7: 104–114, 1987), cartilage matrix protein (CMP) (Paulsson et al., *Biochem. J.* 197: 367–375, 1981; Winterbottom et al., *Dev. Dynamics* 193: 266–276, 1992), fibromodulin (Hedbom et al., *J. Biol. Chem.* 264: 6898–6905, 1989) and collagen binding protein (Chandrasekhar et al., *Proc. Natl. Acad. Sci. USA* 83: 5126–5130, 1986 ), have also been described. The role of these proteins in the organization of the fibrils is not clear, although it has been recently reported that CMP binds to type II collagen (Winterbottom et al., supra).

CMP is a homotrimer of disulfide bond linked subunits, and contains a domain with significant homology to epidermal growth factor, and two homologous repeat sequences (CMP-1 and CMP-2) which have homology to regions within von Willebrand's factor, complement factor B, complement factor C2, Type VI collagen, and the α chains of the integrins Mac-1, p150,95 and LFA-1 (Kiss et al., *J. Biol. Chem.* 264: 8126, 1989; Argraves et al. *Proc. Natl. Acad. Sci. USA* 84: 464, 1987). These repeat sequences have been reported to contain the regions responsible for collagen binding (Winterbottom et al., supra).

Most of the extracellular space between the collagen fibrils is occupied by the second major component of the cartilage extracellular matrix, the ternary complex, which is composed of monomers of the large cartilage proteoglycan, aggrecan, link protein (LP), and hyaluronic acid (HA). The polyanionic glycosaminoglycan side chains of each aggrecan monomer are covalent modifications of the core protein and restrain large volumes of water and ions within the matrix, thus providing the shock-absorbing properties of the cartilage tissue (Hascall, *J. Supramol. Struc.* 7: 101–120, 1970). As many as 100 aggrecan monomers bind to a single HA polymer through amino acid residues contained in the amino-terminal globular domain. These interactions are stabilized by the binding of a single molecule of LP independently to both aggrecan and HA (Hascall, in *Biology of Carbohydrates*, Vol 1., pp. 1–49, ed. Ginsberg, C., Wiley, N.Y., 1981).

The amino acid sequence of LP has revealed that this protein is composed of an $NH_2$-terminal domain which possesses homology with immunoglobulin like proteins (Bonnet et al., *Biochem. Biophys. Acta.* 873: 152, 1986) and two tandemly repeated sequences that have homology with the HA-binding region of aggrecan (Deak et al. *Proc. Acad. Sci. USA* 83: 3766, 1986; Doege et al., *Proc. Acad. Sci. USA* 83; 3761, 1986; Neame et al., *J. Biol. Chem.* 261: 3519, 1986). Based on this sequence homology it has been suggested that these tandemly repeated sequences contain the sites for interaction with HA (Deak et al., supra; Neame et al., *J. Biol. Chem.* 260: 12402, 1985; Goetinck et al., *J. Cell Biol.* 105: 2403, 1987). In addition to being present in large amounts in cartilage, LP has also been found in a number of embryonic tissues including aorta, dorsal skin, kidney, and eyes, as well as in the connective tissue along the entire digestive tract (Gardell et al., *BBRC* 95: 1823, 1980; Stirpe et al., *Dev. Biol.* 137: 419, 1990; Poole et al.,*J. Cell Biol.* 93: 910, 1982; Ripellino et al., *J. Cell Biol.* 108: 1899, 1989; Binette et al., *Mol. Biol. Cell* 3: 224, 1992). It has been proposed that the presence of LP in a wide variety of tissues indicates that this protein may also play a role in the stabilization of the extracellular matrix of non-cartilaginous tissues (Binnette et al., supra).

To date, the nature of the macromolecular interactions between the major components of the extracellular matrix of cartilage and non-cartilaginous tissues are unknown, but it has been recognized that this interaction is critical for the growth and maintenance of these tissues.

SUMMARY OF THE INVENTION

We have discovered that link protein binds to cartilage matrix protein, thus providing the first evidence of a direct interaction between the two major components of the extracellular cartilage matrix. Consequently, in one aspect, the invention features a method for promoting repair of diseased or injured cartilaginous tissue, e.g., in a mammal such as a human patient, by administering a polypeptide capable of promoting the binding of a complex of a proteoglycan (e.g., aggrecan) and hyaluronic acid to collagen.

In preferred embodiments of this aspect of the invention, the administered polypeptide is a fusion polypeptide containing a fragment of cartilage matrix protein and a fragment of link protein. Preferably, the fragment of LP is capable of binding to the proteoglycan-HA complex (and thus includes one or both tandem repeat sequences; at least one of such sequences is required for binding), and the fragment of CMP is capable of binding to collagen. Most preferably, the fusion polypeptide contains CMP-1 or CMP-2 attached to a substantially (at least 90%) full-length LP polypeptide. The polypeptide may be administered to the tissue directly, e.g., by injection in a pharmaceutically acceptable carrier, or by delivering cells containing a recombinant nucleic acid capable of expressing the polypeptide. Preferably, the administered cells are chondrocytes; most preferably the chondrocytes are obtained from the recipient patient, and transfected with the recombinant DNA in culture prior to administration.

In a second aspect, the invention features a method of promoting attachment of cartilaginous tissue to a surface which includes the steps of anchoring to the surface either, (a) cartilage matrix protein; (b) a fragment of cartilage matrix protein capable of binding to collagen and link protein; (c) link protein; (d) a fragment of link protein capable of binding to a complex of proteoglycan and hyaluronic acid and cartilage matrix protein; (e) a fusion polypeptide comprising a fragment of cartilage matrix protein capable of binding to collagen, and a fragment of link protein capable of binding to a complex of hyaluronic acid and a proteoglycan; or (f) a combination of two or more of the polypeptides of (a) through (e); and then contacting the tissue with the surface for a period of time sufficient to allow the attachment to occur.

In one embodiment of the second aspect of the invention the method is used to promote the attachment of cartilage matrix protein to a surface by anchoring to the surface a polypeptide fragment of link protein which is capable of binding to cartilage matrix protein, and then contacting the surface with cartilage matrix protein for a period of time sufficient to allow the attachment to occur. Preferably, the fragment of link protein includes one or both of the tandem repeat amino acid sequences.

In another related embodiment of the second aspect of the invention, the method is used to promote attachment of link protein to a surface by anchoring to the surface a polypeptide fragment of cartilage matrix protein which is capable of binding to link protein, and then contacting the surface with link protein for a period of time sufficient to allow link protein to attach to the surface.

In preferred embodiments of the second aspect of the invention, the polypeptide may be anchored to the surface, e.g., prosthetic device, implant, or tissue graft, by ionic or hydrophobic interactions of the polypeptide with the surface, or by cross-linking the polypeptide to the surface using conventional methods. In another alternative, the polypeptide may be admixed or embedded in a biocompatible composition, e.g., a gel, which may then be used to coat the surface. In still another alternative, cells, e.g., chondrocytes or fibroblasts, containing a recombinant molecule capable of expressing the polypeptide are used to coat or permeate the desired surface.

In a further aspect, the invention features a method for promoting the interaction of collagen with a complex of proteoglycan, hyaluronic acid and link protein in a non-cartilaginous tissue, e.g., skin, by administering to the tissue a polypeptide capable of promoting the binding of the proteoglycan-HA-LP complex to collagen. Preferably, the polypeptide is cartilage matrix protein, or a fragment of cartilage matrix protein which is capable of binding to collagen and link protein. The CMP polypeptide or fragment may be delivered to the tissue by any of the methods described above. In the case, where delivery is mediated by delivery of a CMP transfected cell, the preferred cell type of cell is a fibroblast, e.g., skin fibroblast.

The invention also features a fusion polypeptide, containing a fragment of cartilage matrix protein and a fragment of link protein. Preferably, the fragment of LP is capable of binding to a complex of hyaluronic acid and a proteoglycan; more preferably the fragment includes one or both of the tandem repeat sequences of LP; and most preferably, the fragment includes substantially the whole amino acid sequence of LP. Also preferably, the fragment of CMP is capable of binding collagen; most preferably the fragment of CMP includes CMP-1 or CMP-2 or both CMP-1 and CMP-2.

In another related aspect, the invention features a polypeptide which includes a fragment of link protein that is capable of binding to cartilage matrix protein. In one particularly preferred embodiment, this polypeptide includes one or both of the tandem repeat sequences of link protein.

As used herein, the term "fragment" means at least 10 contiguous amino acids, and preferably at least 20 contiguous amino acids, and may include the entire amino acid sequence of either CMP or LP. Preferable fragments according to the invention are those which exhibit biological activity, i.e., binding characteristics of the native protein as determined by the assays described below. Fragments of CMP and LP can be generated by methods known to those skilled in the art or may result from normal protein processing (e.g., removal of amino acids from the nascent polypeptide that are not required for biological activity or removal of amino acids by alternative mRNA splicing or alternative protein processing events).

The nucleotide sequence of chicken CMP is available from GenBank™/EMBL Data Bank under accession numbers X12346-X12354. The nucleotide sequence of human CMP is available from GenBank™/EMBL Data Bank under accession numbers Jo5666 and JO5667. CMP-1 (the CMP-1 domain) is a sequence corresponding to amino acids 30–220 of chicken CMP; CMP-2 (the CMP-2 domain) is a sequence corresponding to amino acids 262–450 of CMP (numbering according to Kiss et al., supra). CMP-1 also corresponds to amino acids 23 to 222 human CMP, and CMP-2 also corresponds to amino acids 264–453 of human CMP (numbering according to Jenkins et al., supra). The term CMP-1 also includes polypeptides corresponding to domains in proteins such as the von Willebrand factor, complement factor B, complement factor C2, type VI collagen, and the α chains of the integrins Mac-1, p150,95 and LFA-1 that are homologous the to human or chicken CMP-1 domain. The term CMP-2 also includes polypeptides corresponding to domains in proteins such as the von Willebrand factor, complement factor B, complement factor C2, type VI collagen, and the α chains of the integrins Mac-1, p150,95 and LFA-1 that are homologous to the human or chicken CMP-2 domain. Such homologous domains have been identified by standard techniques (see Kiss et al., supra for a review). Such domains are 70% homologous, preferably 80%, more preferably 90% homologous to the human CMP-1 domain or the human CMP-2 domain. Preferably, a CMP fragment is capable of binding to collagen, LP, or to both collagen and LP, with at least 10%, more preferably 30%, and most preferably 70% or more of the binding activity of a full length naturally occurring CMP polypeptide.

The complete amino acid sequence of human link protein is available from GenBank™/EMBL Data Bank under accession number X17405. The complete amino acid sequences of rat chondrosarcoma and chicken LP are also available (Neame et al., supra; Deak et al., supra). The tandem repeat sequences correspond to amino acids 207–226 and 306–325 of chicken LP (numbering according to Deak et al., supra). Preferably, a LP fragment is capable of binding to hyaluronic acid, CMP, or to both hyaluronic acid and CMP with at least 10%, more preferably 30%, and most preferably 70% or more of the binding activity of a full length naturally occurring LP polypeptide.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are now described. All publications mentioned hereunder are incorporated herein by reference. Unless mentioned otherwise, the techniques employed or contemplated herein are standard methodologies well known to one of ordinary skill in the art. The materials, methods and examples are illustrative only and not limiting.

The methods of the invention are useful in the treatment of diseases involving the degeneration of cartilage, e.g., osteoarthritis; for repairing torn cartilage due to any type of trauma, i.e., injury or surgery; and for promoting the adhesion and biocompatibility of prosthetic devices.

Other features and advantages of the invention will be apparent from the following description of the preferred embodiments thereof, and from the claims.

BRIEF DESCRIPTION OF THE DRAWINGS

FIG. 5 depicts the amino acid sequence of human LP (SEQ ID NO:2). The signal peptide is marked between arrows and the two proteoglycan tandem repeats are enclosed in brackets. The domain exhibiting structural homology to the immunoglobulin variable-region fold is underlined.

DETAILED DESCRIPTION OF THE PREFERRED EMBODIMENTS

CMP and LP

Described below are methods for producing CMP and LP, generating CMP and LP fragments, determining the CMP fragments which bind to LP and collagen, determining the LP fragments which bind to CMP, generating fusion proteins of LP and CMP, as well as therapeutic uses of these molecules.

Purification of CMP

Chicken sternal cartilage was purchased from Pelfreeze (Rogers, Ark.), and cleared by dissection of any remaining muscle and perichondrium. The tissue was then ground in a standard coffee grinder at −70° C. with dry ice, and extracted with 4M guanidine-HCl, 50 mM Tris-HCl pH 7.5 by stirring at 4° C. for approximately 2 hours. The extract was subjected to centrifugation at 20,000×g for 20 min to remove insoluble materials and soluble material was applied to an octyl-sepharose column (110 ml bed volume, Pharamcia, Picaway, N.J.) that had been pre-equilibrated with the extraction buffer. The column was washed with extraction buffer until no further protein could be detected in the flow through volume at an absorbance of 280 nm (generally a minimum of 10 column volumes). The bound proteins were eluted with extraction buffer containing 0.5% 3-[(3-cholamindopropyl) dimethyl-ammonio]-1-propanosulfonate (CHAPS). The eluate was concentrated by ultrafiltration in ultrafiltration chambers over YM10 membranes (Amincon, Beverly, Mass.) and then applied to a sephacryl S200 (Pharmacia) column (2.5 cm diameter by 69 cm length) which was run at 1 ml per minute in extraction buffer which did not contain CHAPS. The void volume was collected and concentrated by ultrafiltration as described above. The resultant material is estimated to be more than 95% pure CMP by the presence of a single protein band on a Coomassie blue stained SDS-PAGE gel. For binding assays, the purified CMP was dialyzed with phosphate buffered saline (PBS) or PBS containing 0.05% Tween-20 (PBS-T) and stored at −20° C. until use.

Aliquots of CMP (0.25 μg) were biotinylated with N-hydroxy-succinimide Biotin (NHS-LC-Biotin, Pierce, Rockford, Ill.) essentially according to the manufacturers' instructions. Briefly, the CMP was dialyzed into 50 mM sodium carbonate pH 8.5, and then mixed with 100 =μg of NHS-LC-Biotin in a total reaction volume of 250 μl. The reaction was allowed to proceed at room temperature for 30 min., and the biotinylated-CMP was separated from the unincorporated biotin by applying the reaction mixture to a BioSpin gel filtration column (BioRad, Richmond, Calif.) and collecting the void volume according to the manufacturer's instructions.

Purification of Link Protein

Chicken sternal cartilage as described above was extracted for 24 hours with 4M guanidine-HCl, 50 mM sodium acetate, 10 mM ethylenediamine tetraacetic acid (EDTA), 100 mM 6-amino caproic acid, 10 mm bezamidine-HCl, pH 5.8 at 4° C. The extract was subjected to centrifugation at 20,000×g for 20 min to remove insoluble materials, and then dialyzed against 9 volumes of extraction buffer that lacked guanidine-HCl. The dialysis effectively reduced the concentration of guanidine from 4M to 0.4M. Under these conditions, referred to as associative conditions, the ternary complex of link protein, aggrecan and hyaluronic acid forms. Cesium chloride was then added to a final solution density of 1.64 g/ml and subjected to centrifugation at 36,000 rpm in a Beckman 50Ti rotor at 4° C. for at least 36 hrs to reach density equilibrium. Under these conditions, the ternary complex sediments to the bottom fraction which was then collected. This fraction is essentially free of other cartilage proteins and is referred to as the A1 fraction (associative CsCl gradient fraction #1). The A1 fractions of a number of gradients were pooled, the total volume determined, and diluted with extraction buffer containing 8M guanidine-HCl to bring the final guanidine-HCl concentration to 4M. Under these conditions, referred to as dissociative conditions, the components of the ternary complex are no longer bound to one another. Cesium chloride was then added to a final solution density of 1.52 g/ml, and the sample was subjected to centrifugation at 36,000 rpm in a Beckman 50Ti rotor at 4° C. for at least 36 hours to attain density equilibrium. Under these conditions, aggrecan and other proteoglycans sediment to the bottom of the gradient, hyaluronic acid occupies the middle, and link protein floats at the top. The top fraction from each tube was collected and dialyzed against 8M urea, 50 mM tris-HCl, pH 6.8, and then applied to a DEAE-cellulose (DE52, Whatman, Maidstone, England) column pre-equilibrated with the dialysis buffer. Under these conditions, the link protein flows through the column while any contaminating proteoglycan binds to the DEAE-cellulose. Analysis of the purified link protein by Coomassie stained SDS-PAGE gel indicates the presence of a single band. The purified link protein was concentrated by ultrafiltration as described above, and dialyzed into PBS or PBS-T for the binding assays, or for storage at −20° C. Biotinylated LP was made according to the methods described above.

Peptides

Peptides corresponding to specific amino acid sequences of LP were synthesized using an automated peptide synthesizer (model No. 430A, Applied Biosystems, Inc., Hauppague, N.Y.) equipped with the chemistry provided by the manufacturer. After cleavage form the resin with hydrogen fluoride, the peptides were washed with cold ethyl ether, redissolved in water, and lyophilized. Peptide purity was tested by HPLC on a C-18 column (3.9 mm internal diameter×300 mm, Waters Chromatography Division, Millipore Corp., Milford, Mass.; microBondapark). In every instance the chromatograms gave a single major peak indicating an estimated purity of 90% or greater. The numbering system used in the identification of the peptides is based on that introduced by Deak et al. (*Proc. Natl. Acad. Sci. USA* 83: 3766–3770, 1986) in which the initiation methionine of the 15-amino acid signal peptide is considered as the first residue.

Antibodies

Monoclonal antibodies 1H1 (anti-CMP), 4B6 (anti-LP), and 3H8 (anti-LP) were prepared by immunizing mice with an 8M urea extract of chick embryo sternal cartilage. The urea extracted proteins were dialyzed into PBS, mixed with Freund's complete adjuvant and used to immunize mice according to standard methods. After three booster immunizations the mice were sacrificed and their spleens removed. The spleen cells were fused with a myeloma cell line according to standard methods and the hybridomas thus generated were screened for the presence of antibodies to CMP and LP by standard ELISA assay. Briefly, microtiter plates were coated with either CMP or LP, reacted with hybridoma media, followed by enzyme linked secondary goat-anti-mouse antibodies (BioRad). The positive hybridomas were subcloned to obtain pure clonally derived cell lines. 1H1, and 4B6 and 3H8, were subsequently tested and shown to react with CMP and LP, respectively, by Western blot analyses, immunofluorescence, and immunoprecipitation.

Polyclonal antisera was generated in rabbits against LP peptide $Asp^{306}$-$Arg^{325}$ coupled to Keyhole Limpet Hemocyanin (KLH) by means of N-succinimidyl-3-(pyridylithio)proponate (SPDP) to a cysteine residue introduced at the amino group of $Asp^{306}$ during synthesis of the peptide. The conditions were based on those described by Pierschbacher et al. (*Proc. Natl. Acad. Sci. USA* 80: 1224–1227, 1983). For each immunization 3 mg of peptide was conjugated to 1 mg of KLH with 0.5 mg of SPDP in 1.5 ml of PBS. For the first immunization the mixture was combined with an equal volume of Freund's complete adjuvant.

The anti-LP monoclonal antibody 8A4 (Caterson et al., *J. Biol. Chem.* 260: 11348–11356, 1985) was obtained as a culture supernatant from the Developmental Studies Hybridoma Bank maintained by contract NO-HD-6–2915 from National Institute of Child Health and Human Development (NICHD, Bethesda, Md.).

Goat anti-rabbit and goat anti-mouse IgG alkaline phosphatase conjugates were obtained from BioRad Laboratories (Richmond, Calif.).

Binding Assays

Generally, the material to be immobilized, CMP, LP, or antibodies, was dialyzed in 0.05 M sodium carbonate buffer, pH 9.6. Sixty microliters of the material was then added to each well of a microtiter plate (EIA, Linbro; Flow Laboratories, McLean, Va.) and incubated at room temperature for 1 hr. The plates were washed with PBS and then blocked with 1% bovine serum albumin (BSA) in PBS for 1 hr. The plates were subsequently washed three times with PBS-T. The next layer of material, dissolved in PBS-T, was then added to the wells for 1 hr at room temperature followed by 5 washes with PBS-T. Subsequent layers were added in the same manner. The activity of the alkaline phosphatase linked to the secondary antibody or to streptavidin was measured by adding 60 μl of 100 mM Tris-HCL, 50 mM $MgCl_2$, 100 mM NaCl, pH 9.5, containing the substrates nitroblue tetrazolium (NBT) and 5-bromo-4-chloro-3-indoyl phosphate (BCIP) at concentrations recommended by the manufacturer (BRL, Bethesda, Md.). Absorbance at 405 nm was determined at 5 minute intervals and recorded using a microtitration-plate reader (Titertek Multiskan Plus, Flow Labs Inc., McLean, Va.). The data were collected using the ΔSoft software (Biometallics, Princeton, N.J.).

Results

Binding of LP to CMP. CMP is immobilized directly to the microtiter plate or captured by an immobilized anti-CMP antibody, and LP is added. Bound LP is then detected by a specific anti-LP antibody followed by a secondary enzyme linked antibody, or with enzyme linked streptavidin when LP is biotinylated.

Figure 1:
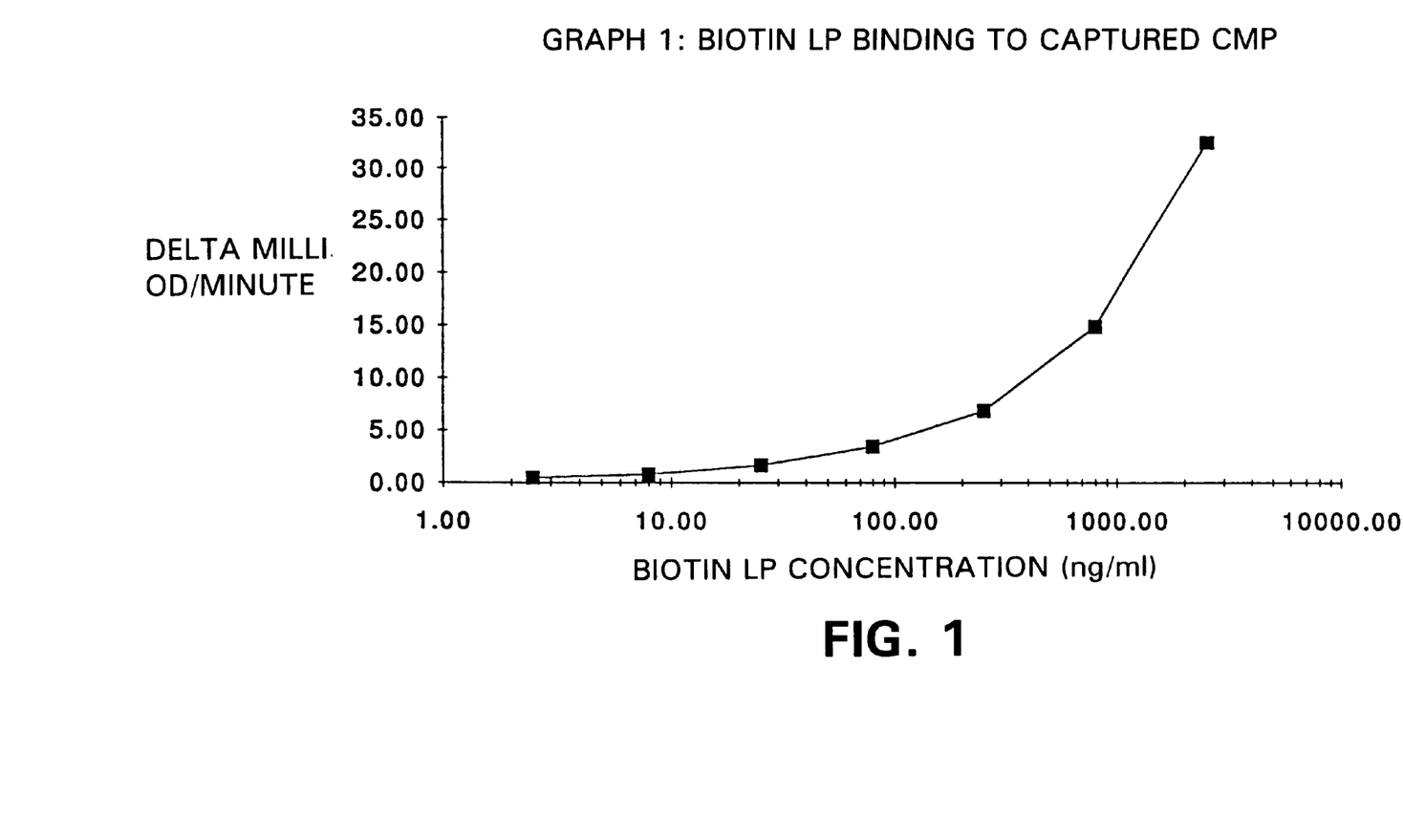
FIG. 1 is a graph which depicts the binding of biotinylated LP to CMP captured by immobilized anti-CMP antibody. The change in optical density (×1000) per minute at 405 nm is plotted as a function of biotinylated LP concentration (ng/ml).

For example, in one assay an anti-CMP monoclonal antibody, 1H1, was immobilized onto each well of a microtiter plate at a concentration of 20 μg/ml, and CMP (0.5 μg/ml) was captured onto the immobilized antibody. Increasing concentrations of biotinylated LP were then added to each well, incubated, and then washed as described above. Biotinylated LP was then detected using alkaline phosphatase coupled streptavidin. The results of this assay, which are shown in FIG. 1, demonstrate that LP binds to CMP in a dose dependent manner.

Binding of CMP to LP. LP is immobilized directly to a microtiter plate or captured by an immobilized anti-LP antibody, and CMP is added. Bound CMP is then detected by a specific anti-CMP antibody followed by a secondary enzyme linked antibody, or with enzyme linked streptavidin when CMP is biotinylated.

Figure 2:
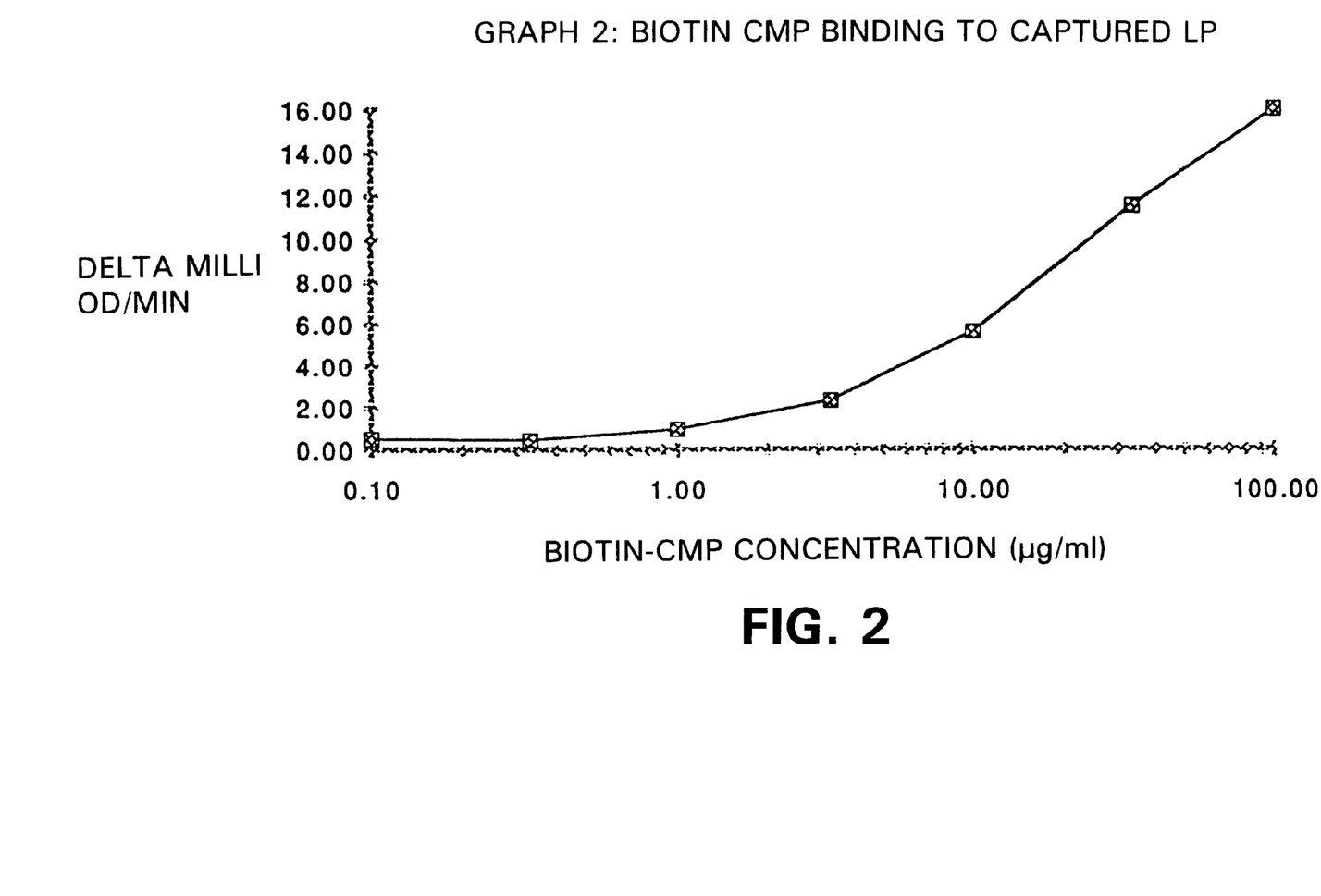
FIG. 2 is a graph which depicts the binding of biotinylated CMP to LP captured by immobilized anti-LP antibody. The change in optical density (×1000) per minute at 405 nm is plotted as a function of biotinylated CMP concentration (μg/ml).

For example, in one assay, micortiter plates were coated with the anti-LP monoclonal antibody, 3H8 (20 μg/ml), and LP (0.5 μg/ml) was captured onto the immobilized antibody. Increasing concentrations of biotinylated CMP were added to each well, incubated, and then washed as described above. Biotinylated CMP was then detected using alkaline phosphatase coupled streptavidin. The results of this assay, which are shown in FIG. 2, demonstrate that CMP binds to LP in a dose dependent manner.

Inhibition of the interaction of LP and CMP. LP is tagged with either monoclonal antibody 4B6 or biotin, and then incubated with increasing amounts of anti-LP antibodies which are directed to specific epitopes on the LP molecule. The mixture is then incubated with CMP immobilized onto microtiter plates, washed, and then detected using either by a secondary enzyme linked antibody, or enzyme linked streptavidin when LP is biotinylated.

Figure 3:
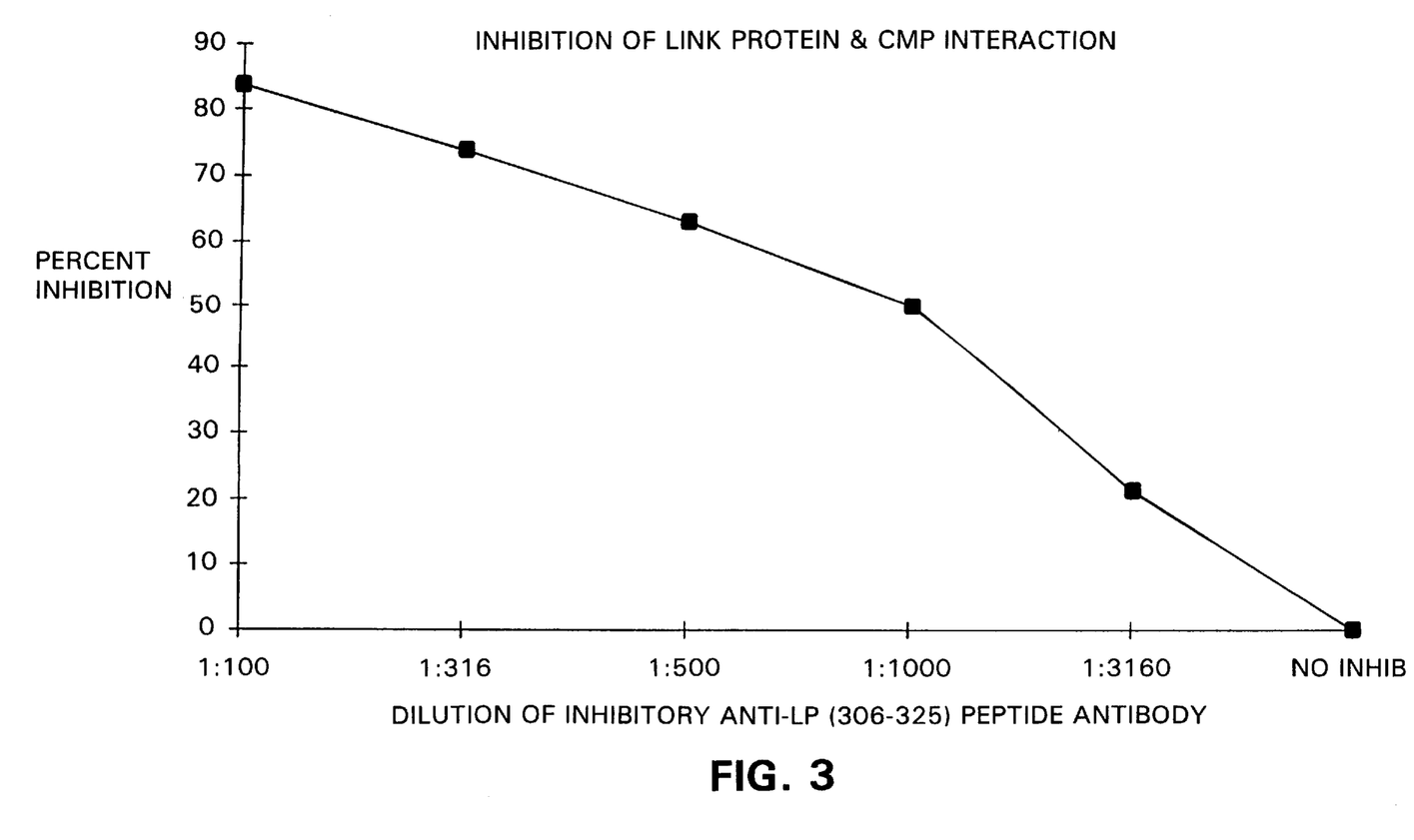
FIG. 3 is a graph which depicts the inhibition of the binding of LP to immobilized CMP by rabbit anti-LP (306–325) peptide antibodies. Percent inhibition is plotted as a function of antibody dilution.
Figure 4:
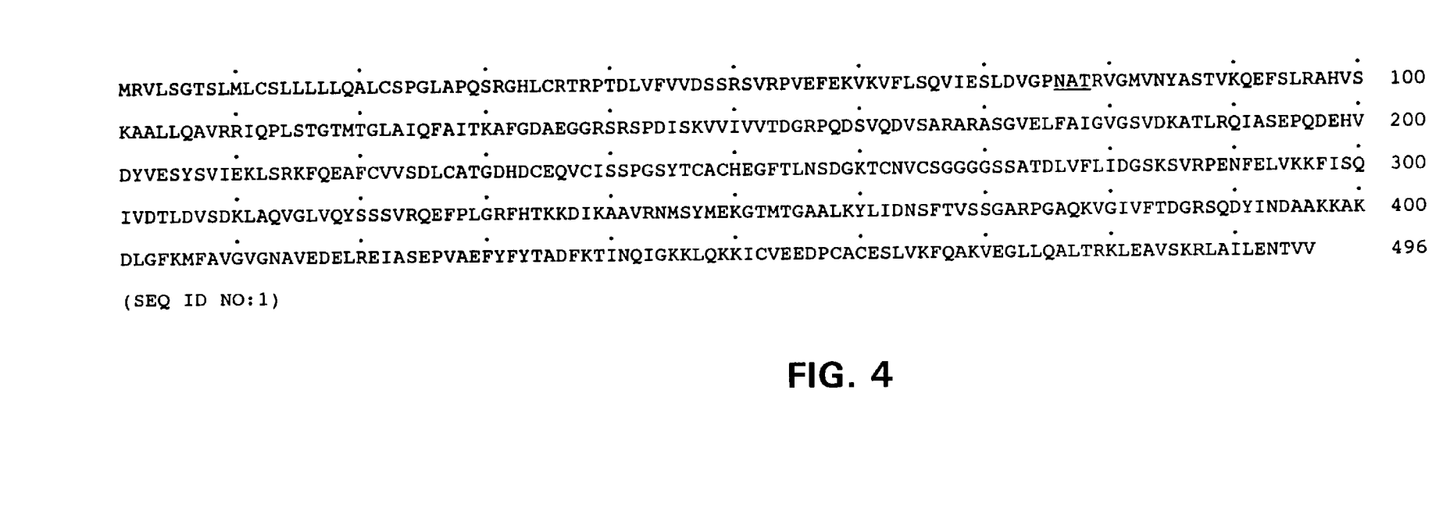
FIG. 4 depicts the amino acid sequence of human CMP (SEQ ID NO:1). Residues are numbered consecutively from the first methionine residue. The mature polypeptide is deduced to begin at the serine(*) at position 23. The site of potential N-glycosylation at position 76–78 is underlined.

The results of one assay, in which LP (3 μg/ml) was tagged with the monoclonal antibody 4B6, and incubated with increasing quantities of rabbit anti-LP(306–325) prior to the incubations with immobilized CMP, are shown in FIG. 3. These results demonstrated that the interaction between LP and CMP is inhibited in a dose dependent manner by the anti-LP(306–325) antibody. The monoclonal antibody, 8A4, which recognizes the LP epitopes $Asn^{207}$-$Pro^{226}$ and $Asp^{306}$-$Arg^{325}$, also inhibits the binding between LP and CMP. Other monoclonal antibodies directed against LP, e.g., 3H8, failed to inhibit this interaction. These results indicate that the binding site on LP involved in the interaction with CMP is in close proximity to one or both of the tandem repeat sequences (amino acid residues 207–226 or 306–325) of chicken LP.

These results indicate that the interaction of the major components of the cartilage extracellular matrix, the ternary complex and the collagen fibril, is mediated, at least in part, by the binding of CMP to LP. Large scale preparation of full length CMP and LP polypeptides, polypeptide fragments, and fusion polypeptides containing various domains of CMP and LP will thus be useful in determining the exact nature of this interaction and the role it plays in promoting cartilage matrix formation.

Fusion Proteins

Fusion proteins containing fragments of CMP, LP, or both may be constructed by standard technology (see, for example, Ausebel et al. supra) using the publically available sequences of the peptides.

For example, one useful method utilizes the maltose binding expression vector system in *E. coli* (New England Biolabs, Beverly, Mass.). In this method, the cDNA of interest is cloned 3' to the maltose binding protein (MBP) of *E. coli* in the vector. Upon induction of the cells with IPTG, the MBP-fusion protein is the predominant protein synthesized by the cells, and can be purified by affinity chromatography on amylose containing resins (New England Biolabs). This expression system has been used to express various fragments of CMP cDNA and may be used to express various fragments of LP as well as fusion polypeptides containing fragments of both CMP and LP. It allows the purification of large quantities of polypeptides, which may then be tested for the ability to bind to various molecules (e.g., collagen, hyaluronic acid, aggrecan, CMP, LP) using the assays described herein. Other *E. coli* vectors such as pGEX (Pharmacia) or pET11 (Novagen, Madison, Wis.) are also useful vectors for expressing large quantities of CMP and LP derived polypeptides.

CMP-LP fusion proteins may also be constructed which bind to both collagen and the proteoglycan-HA complex. Such a fusion may consist of the entire coding region of CMP ligated to the entire coding region of LP. Alternatively, fusion proteins may be constructed containing one or both of the CMP-1 or CMP-2 domains, or smaller fragments of CMP which still retain collagen binding properties as determined by the collagen binding assay described herein. Smaller fragments of LP, e.g., corresponding to the tandem repeat sequences, may also be used which retain the ability to bind to the proteoglycan-HA complex as determined by the assays described herein. The cDNAs encoding the desired sequences from CMP and LP can be generated by conventional means, e.g., polymerase chain reaction using synthetic oligonucleotide primers, and then ligated in a tripartite ligation reaction into an appropriate expression vector. Clones containing the ligated DNA encoding the desired fusion protein in the correct orientation can be screened by hybridization with 20–30 nucleotide oligomers that span the expected ligation sites (using conventional oligomer labelling and hybridization conditions). The CMP-LP fusion constructs may be expressed in *E. coli* in any of the prokaryotic expression vectors described above. For expression in an eukaryotic system, a fusion protein may be constructed containing DNA encoding the signal peptide of LP inserted at the 5' end of a CMP-LP fusion inserted into any appropriate yeast or mammalian expression vector. In addition, CMP-LP fusions may be expressed in in the baculovirus-insect expression system, e.g., using the Blue-Bac II vector (Invitrogen, San Diego, Calif.) in SF-9 cells (ATCC No. CRL1711).

Polypeptide Synthesis and Isolation

Purification of intact LP and CMP polypeptides may be carried out as described above. Alternatively, large scale purification of intact polypeptides, fragments, or fusion polypeptides may be performed using recombinant DNA methods.

In general, polypeptides containing all or part of the amino acid sequence of CMP or LP may be produced by transformation of a suitable host cell with all or part of an CMP or LP-encoding cDNA fragment in a suitable expression vehicle.

Those skilled in the field of molecular biology will understand that any of a wide variety of expression systems may be used to provide any of the recombinant proteins described above. The precise host cell used is not critical to the invention. The polypeptides may be produced in a prokaryotic host (e.g., *E. coli*) or in a eukaryotic host (e.g., *Saccharomyces cerevisiae* or mammalian cells, e.g., CHO and COS). Such cells are available from a wide range of sources (e.g., the American Type Culture Collection, Rockland, Md.; e.g., Ausebel et al., supra). The method of transformation or transfection and the choice of expression vehicle will depend on the host system selected. Transformation and transfection methods are described, e.g., in Ausebel et al., supra; expression vehicles may be chosen from the provided, e.g., in *Cloning Vectors: A Laboratory Manual* (P. H. Pouwels et al., 1985, Supp. 1987).

For example, in one preferred expression system, the cDNA encoding CMP, LP or fragments thereof is inserted into pCDNA1 (Invitrogen, San Diego, Calif.) in an orientation designed to allow expression. This vector provides the cytomegalovirus (CMV) LTR promoter to drive expression of the recombinant polypeptide, a selectable DHFR gene, and SV40 splicing and polyadenylation signals. The vector may be amplified by progressively increasing the concentration of methotrexate in the medium, and has been used to express high levels of CMP cDNA in CHO an COS7 cells. The recombinant polypeptide would be isolated as described above.

Alternatively, LP and CMP polypeptides and fusions may be produced by a stably-transfected mammalian cell line. A number of vectors suitable for stable transfection of mammalian cells are available to the public, e.g., see Pouwels et al., supra; methods for constructing such cell lines are also publically available, e.g., in Ausebel et al., supra. In one example, cDNA encoding an LP or CMP polypeptide is cloned into an expression vector which includes the dihydrofolate reductase (DHFR) gene. Integration of the plasmid and, therefore, the gene into the host cell chromosome is selected for by inclusion of 0.01–300 $\mu$M methotrexate in the cell culture medium (as described in Ausebel et al., supra). This dominant selection can be accomplished in most cell types. Recombinant protein expression can be increased by DHFR-mediated amplification of the transfected gene. Methods for selecting cell lines bearing gene amplifications are described in Ausebel et al., supra; such methods generally involve extended culture in medium containing gradually increasing levels of methotrexate. DHFR-containing expression vectors commonly used for this purpose include pCVSEII and pAdD26SV(A) (described in Ausebel et al., supra). Any of the host cells described above or, preferably, a DHFR-deficient CHO cell line (e.g., CHO DHFR⁻ cells, ATCC Accession No. CRL 9096) are among the host cells preferred for DHFR selection of a stably-transfected cell line or DHFR-mediated gene amplification. In addition, chondrocytes may be obtained from a variety of sources, including the patient to be treated by conventional means (see, for example, Cahn et al., in *Methods in Developmental Biology*, Wilt et al., eds., Thomas Y. Cromwell Co., NY, pp. 493–530, 1967).

Once the recombinant polypeptide is expressed, it may be isolated, e.g., using affinity chromatography. In one example, an anti-CMP antibody may be attached to an column and used to isolate the CMP polypeptide. Lysis and fractionation of CMP or LP harboring cells prior to affinity chromatography may be performed by standard methods (see, e.g., Ausebel et al., supra). Alternatively, a fusion protein, for example a CMP-maltose binding protein, a CMP-β-galactosidase, or a CMP-trpE fusion protein, may be constructed and used for isolation of CMP or LP polypeptides (see, e.g., Ausebel et al., supra; New England Biolabs, Beverly, Mass.).

Once isolated, the recombinant protein can, if desired, be further purified, e.g., by high performance liquid chromatography (see, e.g., Fisher, *Laboratory Techniques in Biochemistry and Molecular Biology*, eds., Work and Burdon, Elsevier, 1980).

Polypeptides of the invention, particularly short CMP or LP fragments, can also be produced by chemical synthesis (e.g., by methods described in *Solid Phase Peptide Synthesis*, 2nd ed., 1084, The Pierce Chemical Co., Rockford, Ill.).

Binding of Polypeptides to Collagen and Proteoglycan-HA Complexes

The binding properties of various CMP and LP polypeptides to proteoglycan-HA complexes and collagen may be analyzed using the assays described above as well as the following assays.

Collagen Binding Assay

This assay is used to determine whether a specific CMP polypeptide or fusion polypeptide is capable of binding collagen. In this assay, microtiter plates are coated with a 1:75 dilution in PBS-T of 2 mg/ml type II collagen (Nitta Gelatin Inc., Osaka, Japan) and dried for ca. 18 hr at 37° C. CMP polypeptides or fusion proteins, purified as described above, are then applied to the collagen coated plates and incubated for 1 hr at 37° C. The polypeptides or fusion proteins are then detected with anti-LP antiserum or anti-CMP antibody (described above) and a secondary antibody essentially as described above.

Fibrillo genesis Assay

This assay is used to determine whether a particular CMP fragment of fusion polypeptide is capable of binding to collagen and promoting fibril formation. The assay is performed essentially as described by Hedbom et al. (*J. Biol. Chem.* 264: 6898, 1989). Briefly, fibrillogenesis is initiated by the addition of type II collagen to fibrillogenesis buffer (60 mM NaCl, 30 mM NaPO$_4$ [pH 7.3]) in the presence or absence of CMP, CPM polypeptides, or fusion polypeptides at 37° C. The final type II collagen concentration is 200 µg/ml, the final polypeptide concentration is 20 µg/ml. Fibrillogenesis is monitored by periodically measuring the optical density of the mixture at 400 nM over the course of several hours.

ELISA for testing interaction of CMP-LP fusion proteins with collaaen and proteoglycan-HA aggregates. In this assay, microtiter plates are coated with type II collagen as previously described. A CMP-LP fusion protein is then applied to the plate and incubated for 1 hr at 37° C. followed by incubation with proteoglycan-HA complexes. The amount of proteoglycan-HA complexes is then quantitated using an antibody to either the proteoglycan or to HA, and an enzyme linked secondary antibody, essentially as described above. The specificity of binding can also be tested by competitive inhibition with soluble LP or CMP.

In an alternative assay, the proteoglycan-HA complexes are immobilized onto microtiter plates, followed by sequential incubations with the CMP-LP fusion protein and collagen. The amount of collagen bound is determined using an anti-collagen antibody (e.g., 1B4, Winterbottem et al., supra) and an enzyme linked secondary antibody. The specificity of the reaction can also be tested by competitive inhibition with soluble LP or CMP.

Use

The interaction of CMP and LP in the formation of the extracellular matrix of cartilaginous tissues indicates that the fusion polypeptides of the invention are useful as therapeutics for halting or delaying the progression of cartilage degeneration in arthritic diseases, and for promoting the rapid growth of cartilage in injured tissues, e.g., joints. The fusion polypeptides may be admixed with a pharmaceutically acceptable carrier substance, e.g., saline, and administered by direct injection at the site of the tissue to promote the binding of collagen fibrils to ternary complexes, thus promoting cartilage matrix formation. Alternatively, the fusion polypeptides may be delivered by injection of cells transfected with recombinant DNA encoding the polypeptide, in a sustained release formulation using a biodegradable biocompatible polymer, or by on-site delivery system using micelles or gels. Dosages of the polypeptides will vary, depending on factors such as the particular mode of delivery chosen, and the condition of the patient.

CMP and LP polypeptides and fragments as well as the fusion polypeptides of the invention are also useful in promoting adherence and biocompatibility of prosthetic devices (e.g., artificial joints, skin) or tissue grafts (e.g., cartilage, skin) used in the surgical repair of tissues containing collagen and proteoglycan complexes. The proteins may be bound to the surface of the prostheses by covalent or ionic interactions according to methods well known to those skilled in the art. In addition, cells expressing one or more of the polypeptides may be used to coat or permeate the prosthetic device prior to delivery. Exact methods of surgical delivery of such prosthetic devices are well known to those skilled in the art.

CMP polypeptides may be delivered to non-cartilaginous tissues to increase the hydration of the tissue, e.g., for cosmetic purposes. Other compounds designed for cosmetic purposes may also be delivered to non-cartilaginous tissue, e.g., skin, by covalent attachment to the CMP, LP or fusion polypeptides used in the methods of the invention.

To effect delivery a compound, e.g., a protein, is generally covalently attached to a polypeptide comprising CMP and/or LP. Many techniques for covalently linking polypeptides are known to those skilled in the art. For example, succinimidyloxycarbonyl-α-methyl-α-(2-pyridyldithio)-toluene and N-succinimidyl 3-(2-pyridyldthio)propionate (Pierce, Rockford, Ill.) are heterobifunctional cross-linkers which can be used to link proteins in a step-wise fashion avoiding the formation of homopolymers and other undesirable side reactions. Alternatively genetically-engineered fusion proteins can be created to link CMP or LP and a protein to be delivered to cartilaginous or collagenous tissue.

In addition, CMP and LP polypeptides and fusion proteins of the invention may be used to promote cartilage matrix formation in vitro, thus providing material for restorative surgery of cartilage in joints, or in cosmetic surgery of tissues containing cartilage (e.g., nose, palate).

Other Embodiments

Other embodiments are within the following claims. For example, analogs of any naturally occurring LP or CMP polypeptide may also be used in the methods of the invention. Analogs can differ from the naturally occurring polypeptides by amino acid sequence differences, by post-translational modifications, or by both. Analogs of the invention will generally exhibit at least 70%, more preferably 80%, even more preferable 90%, and most preferably 95% or even 99%, homology with all or part of a naturally occurring LP or CMP sequence. The length of comparison sequences will be at least 8 amino acid residues, preferably at least 24 amino acid residues, and more preferably more than 35 amino acid residues. Modifications include in vivo and in vitro chemical derivitization of polypeptides, e.g., acetylation, carboxylation, phosphorylation, or glycosylation; such modifications may occur during polypeptide synthesis or processing or following treatment with isolated modifying enzymes. Analogs can also differ form the naturally occurring LP or CMP polypeptides by alterations in primary sequence. These include genetic variants, both natural an induced (for example, resulting from random mutagenesis by irradiation or exposure to ethanemethylsulfate, or by site-specific mutagenesis, e.g., see Sambrook et al., *Molecular Cloning: A Laboratory Manual,* 2d ed., CSH Press, 1989; or Ausebel et al., supra). Also included are cylclized peptide molecules and analogs which contain other than L-amino acids, e.g., D-amino acids or non-naturally occurring or synthetic amino acids, e.g., β or γ amino acids.

We claim:

1. A fusion polypeptide comprising a fragment of cartilage matrix protein which includes a homologous repeat sequence of CMP-1 or CMP-2 and which can bind link protein and collagen, and a fragment of link protein which can bind cartilage matrix protein.

2. The fusion polypeptide of claim 1 wherein said fragment of link protein is capable of binding to a complex of hyaluronic acid and a proteoglycan.

3. The fusion polypeptide of claim 1, wherein said fragment of cartilage matrix protein is a fragment of human cartilage matrix protein and said fragment of link protein is a fragment of human link protein.

4. The fusion polypeptide of claim 1, wherein said fragment of link protein is a fragment of human link protein.

* * * * *

SEQUENCE LISTING (1) GENERAL INFORMATION:

(iii) NUMBER OF SEQUENCES: 2

(2) INFORMATION FOR SEQ ID NO:1:

(i) SEQUENCE CHARACTERISTICS:
       (A) LENGTH: 496 amino acids
       (B) TYPE: amino acid
       (D) TOPOLOGY: linear (ii) MOLECULE TYPE: peptide (xi) SEQUENCE DESCRIPTION: SEQ ID NO:1:

```
Met Arg Val Leu Ser Gly Thr Ser Leu Met Leu Cys Ser Leu Leu Leu
1               5                   10                  15

Leu Leu Gln Ala Leu Cys Ser Pro Gly Leu Ala Pro Gln Ser Arg Gly
            20                  25                  30

His Leu Cys Arg Thr Arg Pro Thr Asp Leu Val Phe Val Val Asp Ser
            35                  40                  45

Ser Arg Ser Val Arg Pro Val Glu Phe Glu Lys Val Lys Val Phe Leu
    50                  55                  60

Ser Gln Val Ile Glu Ser Leu Asp Val Gly Pro Asn Ala Thr Arg Val
65                  70                  75                  80

Gly Met Val Asn Tyr Ala Ser Thr Val Lys Gln Glu Phe Ser Leu Arg
                85                  90                  95

Ala His Val Ser Lys Ala Ala Leu Leu Gln Ala Val Arg Arg Ile Gln
            100                 105                 110

Pro Leu Ser Thr Gly Thr Met Thr Gly Leu Ala Ile Gln Phe Ala Ile
            115                 120                 125

Thr Lys Ala Phe Gly Asp Ala Glu Gly Gly Arg Ser Arg Ser Pro Asp
        130                 135                 140

Ile Ser Lys Val Val Ile Val Val Thr Asp Gly Arg Pro Gln Asp Ser
145                 150                 155                 160

Val Gln Asp Val Ser Ala Arg Ala Arg Ala Ser Gly Val Glu Leu Phe
                165                 170                 175

Ala Ile Gly Val Gly Ser Val Asp Lys Ala Thr Leu Arg Gln Ile Ala
            180                 185                 190

Ser Glu Pro Gln Asp Glu His Val Asp Tyr Val Glu Ser Tyr Ser Val
        195                 200                 205
```

| Ile | Glu | Lys | Leu | Ser | Arg | Lys | Phe | Gln | Glu | Ala | Phe | Cys | Val | Val | Ser |
|---|---|---|---|---|---|---|---|---|---|---|---|---|---|---|---|
| | | 210 | | | | 215 | | | | 220 | | | | | |

Asp Leu Cys Ala Thr Gly Asp His Asp Cys Glu Gln Val Cys Ile Ser
225             230             235             240

Ser Pro Gly Ser Tyr Thr Cys Ala Cys His Glu Gly Phe Thr Leu Asn
        245             250             255

Ser Asp Gly Lys Thr Cys Asn Val Cys Ser Gly Gly Gly Ser Ser
    260             265             270

Ala Thr Asp Leu Val Phe Leu Ile Asp Gly Ser Lys Ser Val Arg Pro
275             280             285

Glu Asn Phe Glu Leu Val Lys Lys Phe Ile Ser Gln Ile Val Asp Thr
290             295             300

Leu Asp Val Ser Asp Lys Leu Ala Gln Val Gly Leu Val Gln Tyr Ser
305             310             315             320

Ser Ser Val Arg Gln Glu Phe Pro Leu Gly Arg Phe His Thr Lys Lys
            325             330             335

Asp Ile Lys Ala Ala Val Arg Asn Met Ser Tyr Met Glu Lys Gly Thr
            340             345             350

Met Thr Gly Ala Ala Leu Lys Tyr Leu Ile Asp Asn Ser Phe Thr Val
        355             360             365

Ser Ser Gly Ala Arg Pro Gly Ala Gln Lys Val Gly Ile Val Phe Thr
370             375             380

Asp Gly Arg Ser Gln Asp Tyr Ile Asn Asp Ala Ala Lys Lys Ala Lys
385             390             395             400

Asp Leu Gly Phe Lys Met Phe Ala Val Gly Val Gly Asn Ala Val Glu
            405             410             415

Asp Glu Leu Arg Glu Ile Ala Ser Glu Pro Val Ala Glu His Tyr Phe
            420             425             430

Tyr Thr Ala Asp Phe Lys Thr Ile Asn Gln Ile Gly Lys Lys Leu Gln
            435             440             445

Lys Lys Ile Cys Val Glu Glu Asp Pro Cys Ala Cys Glu Ser Leu Val
450             455             460

Lys Phe Gln Ala Lys Val Glu Gly Leu Leu Gln Ala Leu Thr Arg Lys
465             470             475             480

Leu Glu Ala Val Ser Lys Arg Leu Ala Ile Leu Glu Asn Thr Val Val
            485             490             495

(2) INFORMATION FOR SEQ ID NO:2:

(i) SEQUENCE CHARACTERISTICS:
        (A) LENGTH: 1400 base pairs
        (B) TYPE: nucleic acid
        (C) STRANDEDNESS: single
        (D) TOPOLOGY: linear     (xi) SEQUENCE DESCRIPTION: SEQ ID NO:2:

```
AAGCAGGCTC CAGGATCAGG ACCTCTGCCA TCCAGCGCCA CAAAGAGACA TTCTACACAC      60

ACTCACACAC ACACACACAC ACACGCACTC TCACACTCGC CCAGAGACAA ACTTAAGGTG     120

AGGAGAAAGA GCGCTAGCTT CACTTGATCT CCAGCTTCCA ACTTAAGCAG AACTTGAGAG     180

CATCCGAACT CCTGGATTTC AGGACAAGTG AAGAAGATTC TTTGGGCTAT AAAG ATG       237
                                                             Met
                                                              1

AAG AGT CTA CTT CTT CTG GTG CTG ATT TCA ATC TGC TGG GCT GAT CAT       285
Lys Ser Leu Leu Leu Leu Val Leu Ile Ser Ile Cys Trp Ala Asp His
  5                   10                  15
```

```
CTT TCA GAC AAC TAT ACT CTG GAT CAT GAC AGA GCT ATT CAC ATC CAA       333
Leu Ser Asp Asn Tyr Thr Leu Asp His Asp Arg Ala Ile His Ile Gln
        20                  25                  30

GCA GAA AAT GGC CCC CAT CTA CTT GTG GAA GCA GAG CAA GCC AAG GTG       381
Ala Glu Asn Gly Pro His Leu Leu Val Glu Ala Glu Gln Ala Lys Val
        35                  40                  45

TTT TCA CAC AGA GGT GGC AAT GTT ACA CTG CCA TGT AAA TTT TAT CGA       429
Phe Ser His Arg Gly Gly Asn Val Thr Leu Pro Cys Lys Phe Tyr Arg
50                  55                  60                  65

GAC CCT ACA GCA TTT GGC TCA GGA ATC CAT AAA ATC CGA ATT AAG TGG       477
Asp Pro Thr Ala Phe Gly Ser Gly Ile His Lys Ile Arg Ile Lys Trp
                70                  75                  80

ACC AAG CTA ACT TCG GAT TAC CTC AAG GAA GTG GAT GTT TTT GTT TCC       525
Thr Lys Leu Thr Ser Asp Tyr Leu Lys Glu Val Asp Val Phe Val Ser
                    85                  90                  95

ATG GGA TAC CAC AAA AAA ACC TAT GGA GGC TAC CAG GGT AGA GTG TTT       573
Met Gly Tyr His Lys Lys Thr Tyr Gly Gly Tyr Gln Gly Arg Val Phe
                100                 105                 110

CTG AAG GGA GGC AGT GAT AGT GAT GCT TCT CTG GTC ATC ACA GAG GTC       621
Leu Lys Gly Gly Ser Asp Ser Asp Ala Ser Leu Val Ile Thr Glu Val
        115                 120                 125

ACT CTG GAA GAT TAT GGG AGA TAT AAG TGT GAG GTG ATT GAA GGA TTA       669
Thr Leu Glu Asp Tyr Gly Arg Tyr Lys Cys Glu Val Ile Glu Gly Leu
130                 135                 140                 145

GAA GAT GAT ACT GTT GTG GTA GCA CTG GAC TTA CAA GGT GTG GTA TTC       717
Glu Asp Asp Thr Val Val Val Ala Leu Asp Leu Gln Gly Val Val Phe
                150                 155                 160

CCT TAC TTT CCA CGA CTG GGG CGC TAC AAT CTC AAT TTT CAC GAG GCG       765
Pro Tyr Phe Pro Arg Leu Gly Arg Tyr Asn Leu Asn Phe His Glu Ala
                165                 170                 175

CAG CAG GCC TGT CTG GAC CAG GAT GCT GTG ATC GCC TCC TTC GAC CAG       813
Gln Gln Ala Cys Leu Asp Gln Asp Ala Val Ile Ala Ser Phe Asp Gln
        180                 185                 190

CTG TAC GAC GCC TGG CGG GGC GGG CTG GAC TGG TGC AAT GCC GGC TGG       861
Leu Tyr Asp Ala Trp Arg Gly Gly Leu Asp Trp Cys Asn Ala Gly Trp
        195                 200                 205

CTC AGT GAT GGC TCT GTG CAA TCT CCC ATC ACA AAG CCC AGA GAG CCC       909
Leu Ser Asp Gly Ser Val Gln Ser Pro Ile Thr Lys Pro Arg Glu Pro
210                 215                 220                 225

TGT GGG GGC CAG AAC ACA GTG CCC GGA GTC AGG AAC TAC GGA TTT TGG       957
Cys Gly Gly Gln Asn Thr Val Pro Gly Val Arg Asn Tyr Gly Phe Trp
                230                 235                 240

GAT AAA GAT AAA AGC AGA TAT GAT GTT TTC TGT TTT ACA TCC AAT TTC       1005
Asp Lys Asp Lys Ser Arg Tyr Asp Val Phe Cys Phe Thr Ser Asn Phe
            245                 250                 255

AAT GGC CGT TTT TAC TAT CTG ATC CAC CCC ACC AAA CTG ACC TAT GAT       1053
Asn Gly Arg Phe Tyr Tyr Leu Ile His Pro Thr Lys Leu Thr Tyr Asp
        260                 265                 270

GAA GCG GTG CAA GCT TGT CTC AAT GAT GGT GCT CAG ATT GCA AAA GTG       1101
Glu Ala Val Gln Ala Cys Leu Asn Asp Gly Ala Gln Ile Ala Lys Val
    275                 280                 285

GGC CAG ATA TTT GCT GCC TGG AAA ATT CTC GGA TAT GAC CGC TGT GAT       1149
Gly Gln Ile Phe Ala Ala Trp Lys Ile Leu Gly Tyr Asp Arg Cys Asp
290                 295                 300                 305

GCG GGC TGG TTG GCG GAT GGC AGC GTC CGC TAC CCC ATC TCT AGG CCA       1197
Ala Gly Trp Leu Ala Asp Gly Ser Val Arg Tyr Pro Ile Ser Arg Pro
                310                 315                 320

AGA AGG CGC TGC AGT CCT ACT GAG GCT GCA GTG CGC TTC GTG GGT TTT       1245
Arg Arg Arg Cys Ser Pro Thr Glu Ala Ala Val Arg Phe Val Gly Phe
                325                 330                 335
```

| | |
|---|---|
| CCA GAT AAA AAG CAT AAG CTG TAT GGT GTC TAC TGC TTC AGA GCA TAC<br>Pro Asp Lys Lys His Lys Leu Tyr Gly Val Tyr Cys Phe Arg Ala Tyr<br>        340                   345               350 | 1293 |
| AAC TGAATGTGCC CTTAGAGCGC ACTAGTTTAA GTCAATTAAG ACATGTGAAG<br>Asn | 1346 |
| GTGTTTTTTT CCAATATGAA CTCATGCAAG TTACCAAACT TGATACCTTT TTAC | 1400 |